(12) United States Patent
Frazier et al.

(10) Patent No.: US 6,469,138 B1
(45) Date of Patent: Oct. 22, 2002

(54) THROMBOSPONDIN RECEPTOR BINDING PEPTIDES

(75) Inventors: William A. Frazier, St. Louis, MO (US); Minh D. Kosfeld, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 08/391,820

(22) Filed: Feb. 21, 1995

Related U.S. Application Data

(62) Division of application No. 08/029,333, filed on Mar. 5, 1993, now Pat. No. 5,399,667.

(51) Int. Cl.[7] .................................................. C07K 5/08
(52) U.S. Cl. ........................................ 530/330; 514/17
(58) Field of Search .............................. 514/17; 530/330

(56) References Cited

U.S. PATENT DOCUMENTS

| | | | | |
|---|---|---|---|---|
| 4,847,201 A | * | 7/1989 | Kaswasaki | 435/70 |
| 4,882,145 A | * | 11/1989 | Thornton | 424/88 |
| 5,155,038 A | | 10/1992 | Eyal et al. | 435/240.2 |
| 5,190,918 A | | 3/1993 | Deutch et al. | 514/15 |
| 5,190,920 A | | 3/1993 | Baltimore et al. | 514/17 |
| 5,192,744 A | | 3/1993 | Bouck et al. | 514/8 |
| 5,200,397 A | | 4/1993 | Deutch et al. | 514/15 |

FOREIGN PATENT DOCUMENTS

WO        9217499     10/1992

OTHER PUBLICATIONS

Tashiro, J. Biol. Chem 264, 16174, 1989.*
Kosfeld & Frazier, J. Biol. Chem. 267, pp 16230–16236 (1992).
Kosfeld et al., J. Biol. Chem. 266, pp 24257–24259 (1991).
Dixit et al., Proc. Natl. Acad. Sci. 82, 3472–3476 (1985).
Kosfeld & Frazier, J. Biol. Chem. 268, 8808–8814 (1993).

* cited by examiner

*Primary Examiner*—Christopher S. F. Low
*Assistant Examiner*—David Lukton
(74) *Attorney, Agent, or Firm*—Scott J. Meyer

(57) ABSTRACT

Novel short peptides are described that bind to the thrombospondin 1 receptor, which preferably have five amino acid residues which share the tetrapeptide Arg-Val-Ala-Val and have the following sequences:

Figure 4:
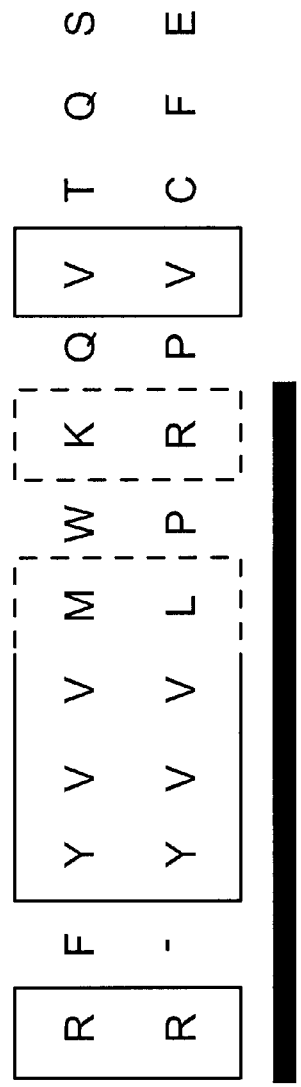
Figure 4:
Figure 4:
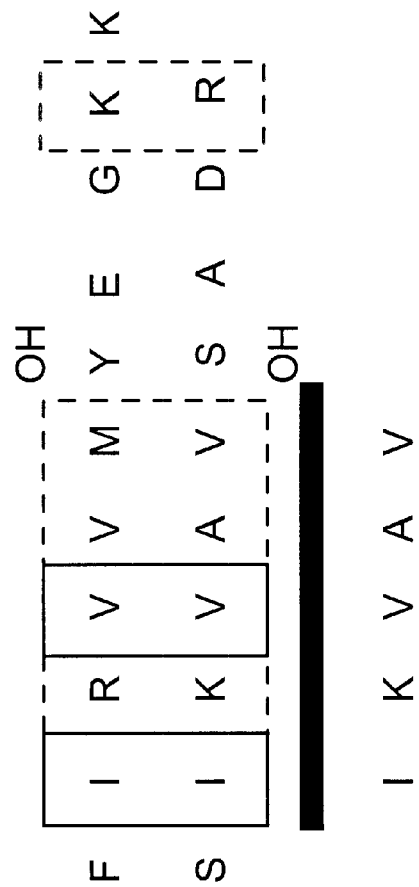
Figure 4:

Ile-Arg-Val-Ala-Val [SEQ ID NO:13] and
Val-Arg-Val-Ala-Val [SEQ ID NO:14].

2 Claims, 9 Drawing Sheets

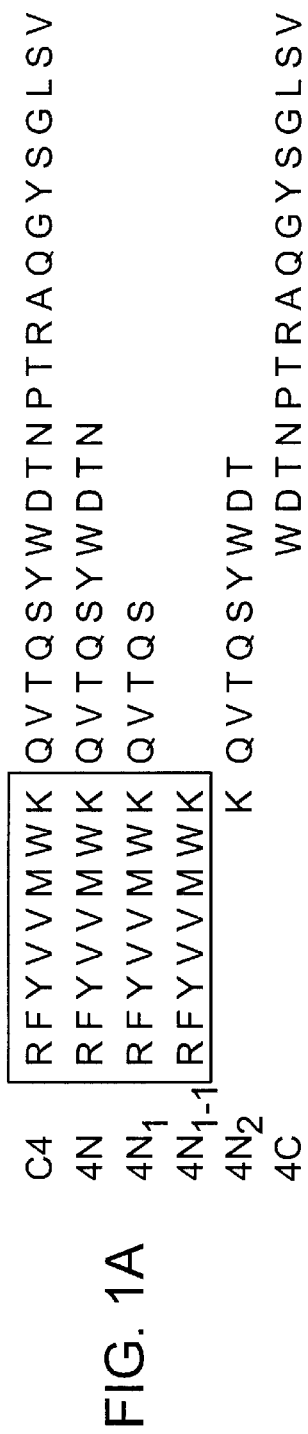
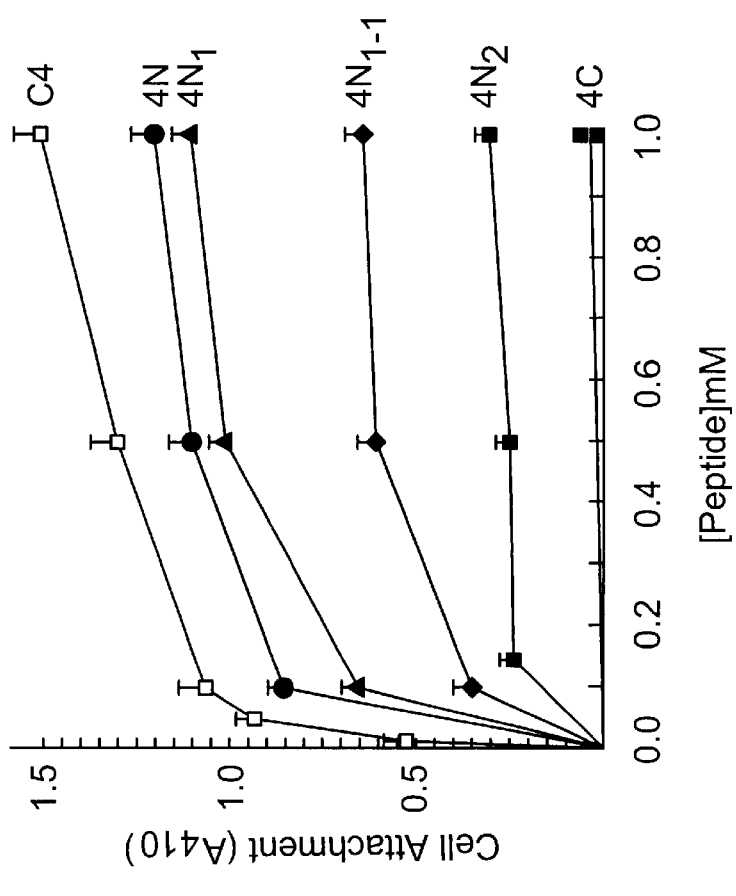
FIG. 1A
FIG. 1B

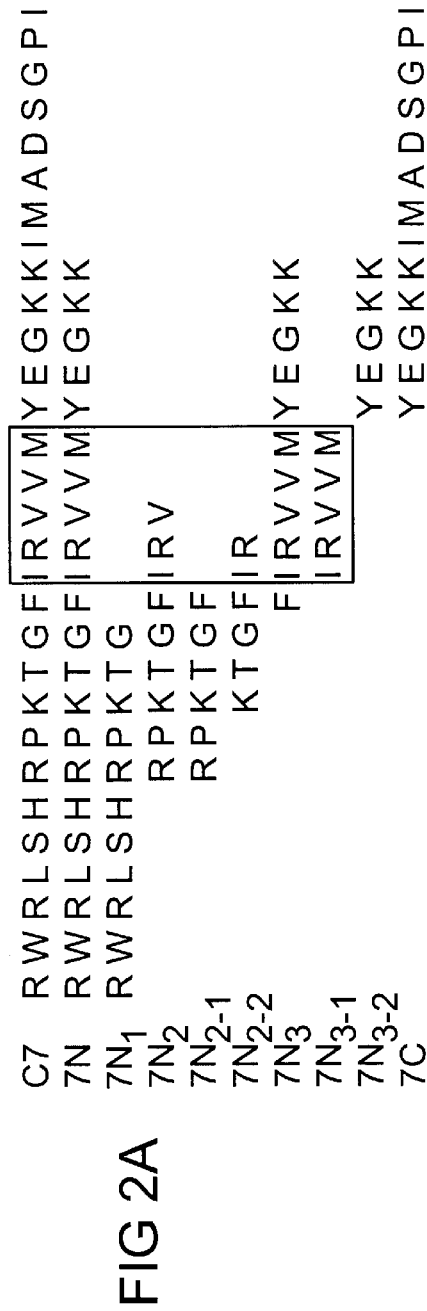
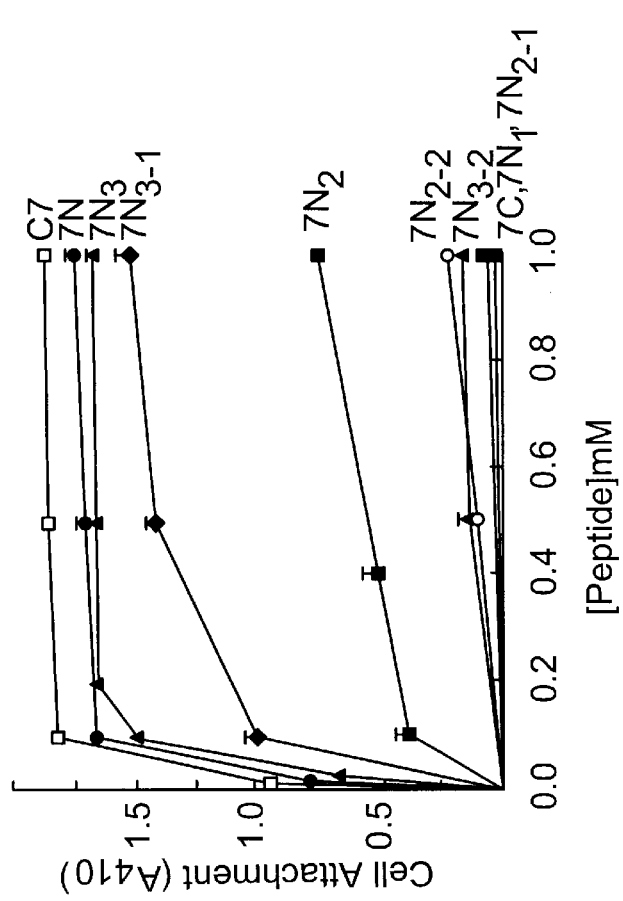
FIG 2A
FIG 2B

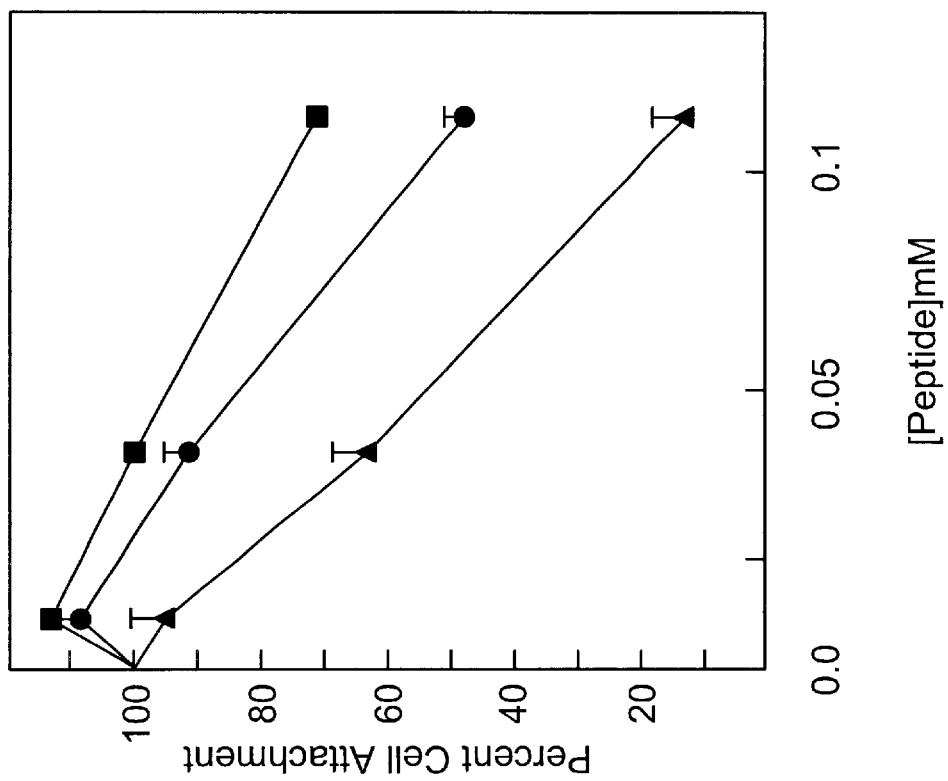
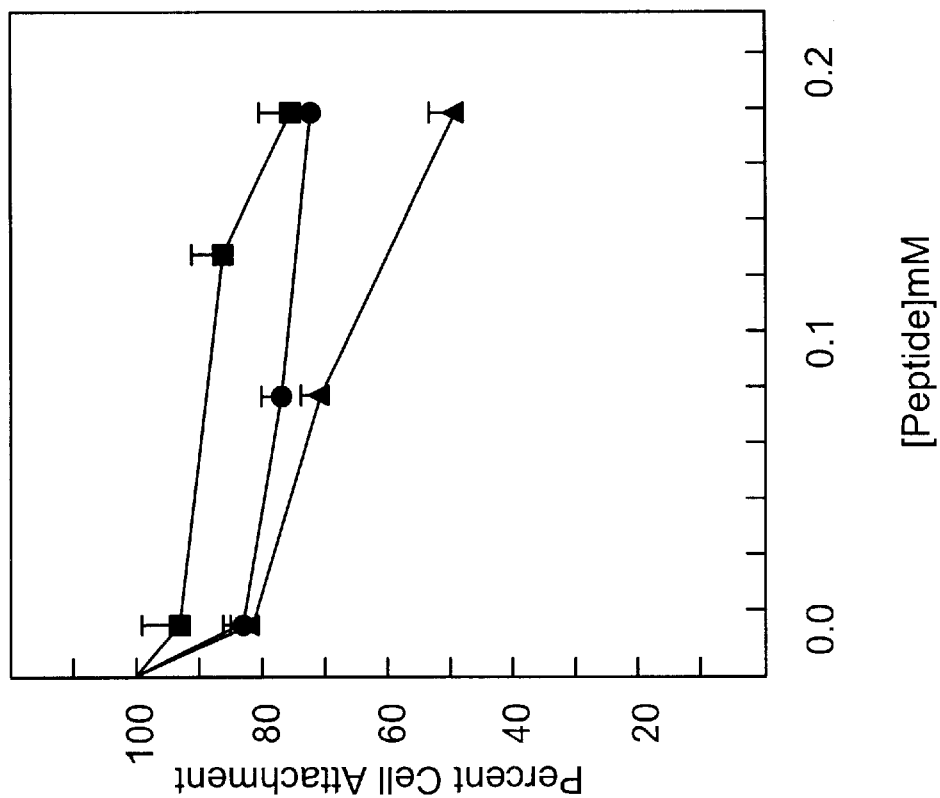
FIG. 3A
FIG. 3B

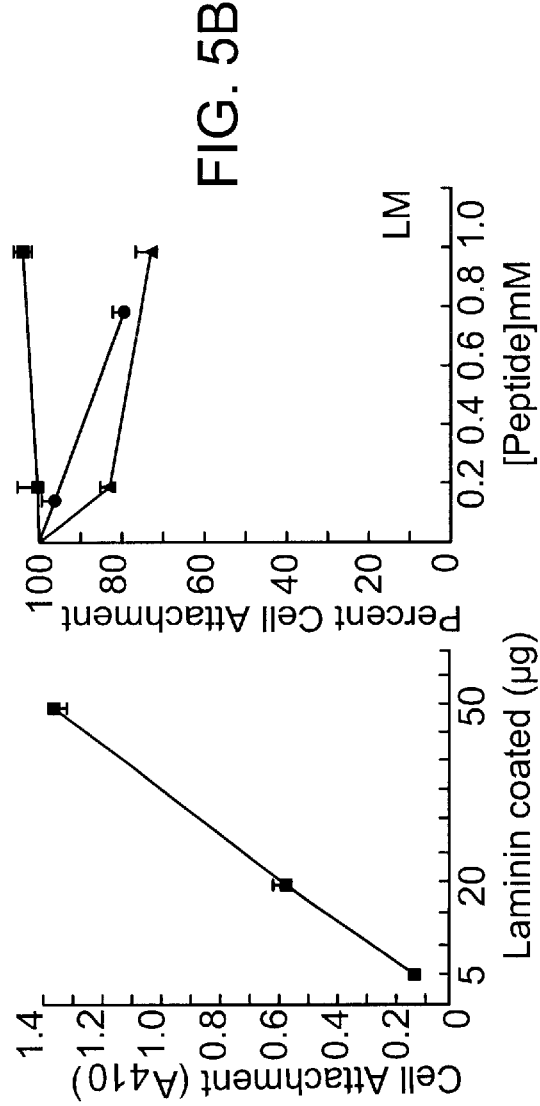
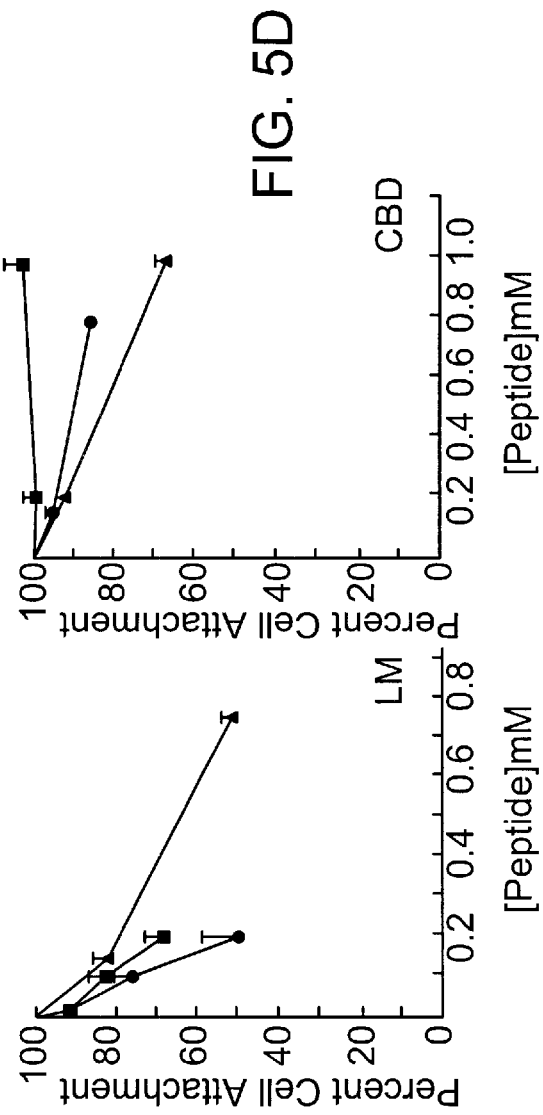
FIG. 5A
FIG. 5B
FIG. 5C
FIG. 5D

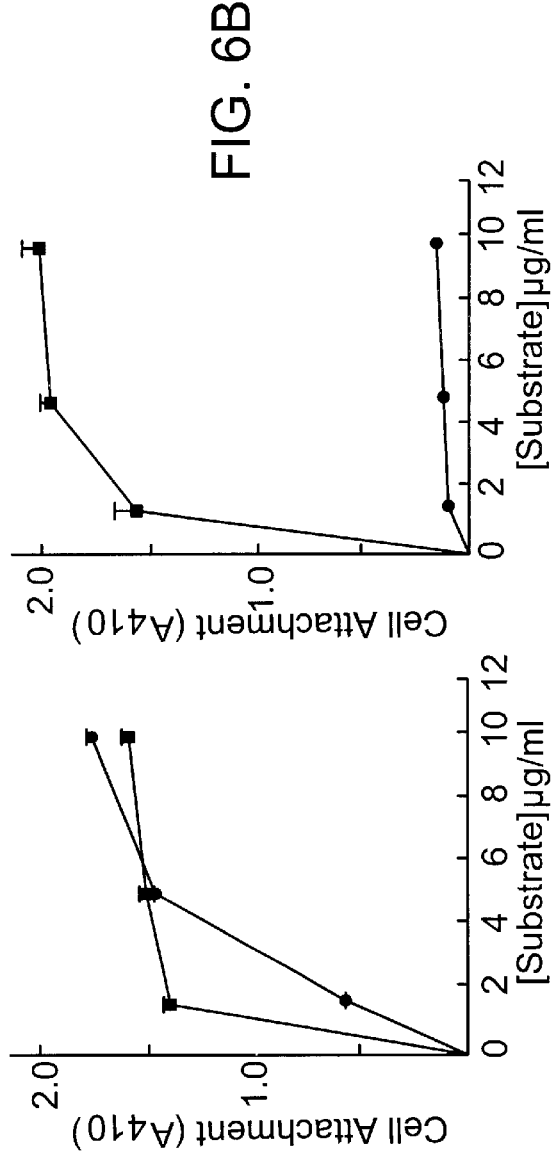
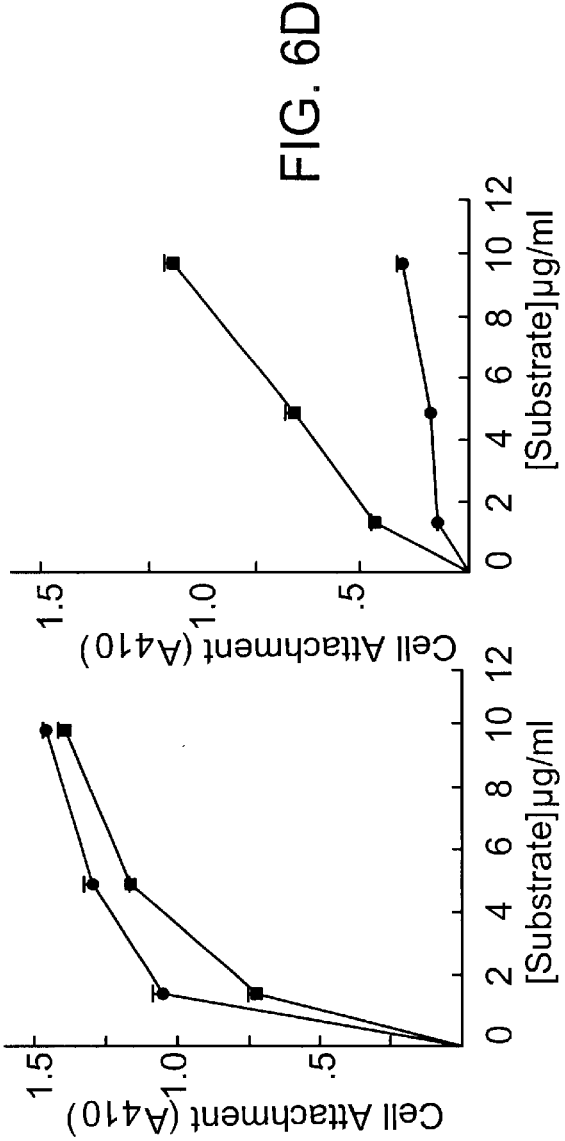
FIG. 6A
FIG. 6B
FIG. 6C
FIG. 6D

FIG. 8A

Peptide 7N-3 Homologs in TS Isoforms

| | | | | | | | | | |
|---|---|---|---|---|---|---|---|---|---|
| HUMAN-1 | F | I | R | V | V | M | Y | E | G | K | K |
| MOUSE-1 | Y | I | R | V | V | M | Y | E | G | K | K |
| HUMAN-2 | Y | I | R | V | L | V | H | E | G | K | Q |
| MOUSE-2 | Y | M | R | V | L | V | H | E | G | K | Q |
| CHICKEN-2 | L | I | K | V | L | V | Y | E | G | K | Q |
| MOUSE-3 | Y | I | R | V | K | L | Y | E | G | P | Q |
| COMP | Y | I | R | V | R | F | Y | E | G | P | E |

FIG. 8B

Peptide 4N-1 Homologs in TS Isoforms

| | | | | | | | | | |
|---|---|---|---|---|---|---|---|---|---|
| HUMAN-1 | R | F | Y | V | V | M | W | K | Q | V | T |
| MOUSE-1 | R | F | Y | V | V | M | W | K | Q | V | T |
| HUMAN-2 | R | F | Y | V | V | M | W | K | Q | V | T |
| MOUSE-2 | R | F | Y | V | V | M | W | K | Q | V | T |
| CHICKEN-2 | R | F | Y | V | L | M | W | K | Q | T | E |
| MOUSE-3 | R | F | Y | V | V | M | W | K | Q | V | T |
| COMP | S | F | Y | V | V | M | W | K | Q | M | E |

FIG. 9A  TENASCIN

Human/Mouse TS-1 7N3   F I R V - V M Y E G K K
Human/Mouse Tenascin    F I R V F A I L E N K K

FIG. 9B  SERUM PROTEINS

Human/Mouse TS-1              I R V V M
Human/Mouse Laminin A         I K V A V

Porcine vWF, Factor VIII      I R V A V
Rat α-2 Macroglobulin

Human vWF                     V R V A V

SEQUENCE LISTING (1) GENERAL INFORMATION:

(iii) NUMBER OF SEQUENCES: 47

(2) INFORMATION FOR SEQ ID NO: 1:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 1:

Arg Phe Tyr Val Val Met Trp Lys Gln Val Thr Gln Ser
1               5                   10

(2) INFORMATION FOR SEQ ID NO: 2:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 2:

Arg Phe Tyr Val Val Met Trp Lys
1               5

(2) INFORMATION FOR SEQ ID NO: 3:

(i) SEQUENCE CHARACTERISTICS:
        (A) LENGTH: 6 amino acids

```
        (B) TYPE: amino acid
        (D) TOPOLOGY: linear (ii) MOLECULE TYPE: peptide (xi) SEQUENCE DESCRIPTION: SEQ ID NO: 3:

Arg Phe Tyr Val Val Met
1               5

(2) INFORMATION FOR SEQ ID NO: 4:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 4:

Phe Ile Arg Val Val Met Tyr Glu Gly Lys Lys
1               5                   10

(2) INFORMATION FOR SEQ ID NO: 5:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 5:

Ile Arg Val Val Met
1               5

(2) INFORMATION FOR SEQ ID NO: 6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 6:

Gly Arg Val Val Met
1               5

(2) INFORMATION FOR SEQ ID NO: 7:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 7:

Ile Glu Val Val Met
1               5

(2) INFORMATION FOR SEQ ID NO: 8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide
```

(xi) SEQUENCE DESCRIPTION: SEQ ID NO: 8:

Ile Arg Val Val Gly
1               5

(2) INFORMATION FOR SEQ ID NO: 9:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 9:

Leu Gly Thr Ile Pro Gly
1               5

(2) INFORMATION FOR SEQ ID NO: 10:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 10:

Pro Gly Ala Ile Pro Gly
1               5

(2) INFORMATION FOR SEQ ID NO: 11:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 11:

Tyr Ile Gly Ser Arg
1               5

(2) INFORMATION FOR SEQ ID NO: 12:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 12:

Ile Lys Val Ala Val
1               5

(2) INFORMATION FOR SEQ ID NO: 13:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO: 13:

Ile Arg Val Ala Val

```
1               5
```

(2) INFORMATION FOR SEQ ID NO: 14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO: 14:

```
Val Arg Val Ala Val
1               5
```

(2) INFORMATION FOR SEQ ID NO: 15:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 15:

```
Arg Phe Tyr Val Val Met Trp Lys Gln Val Thr Gln Ser Tyr Trp Asp
1               5                   10                  15
Thr Asn Pro Thr Arg Ala Gln Gly Tyr Ser Gly Leu Ser Val
            20                  25                  30
```

(2) INFORMATION FOR SEQ ID NO: 16:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 16:

```
Arg Phe Tyr Val Val Met Trp Lys Gln Val Thr Gln Ser Tyr Trp Asp
1               5                   10                  15
Thr Asn
```

(2) INFORMATION FOR SEQ ID NO: 17:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 17:

```
Lys Gln Val Thr Gln Ser Tyr Trp Asp Thr
1               5                   10
```

(2) INFORMATION FOR SEQ ID NO: 18:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 18:

```
Trp Asp Thr Asn Pro Thr Arg Ala Gln Gly Tyr Ser Gly Leu Ser Val
1               5                  10                  15
```

(2) INFORMATION FOR SEQ ID NO: 19:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 19:

```
Arg Trp Arg Leu Ser His Arg Pro Lys Thr Gly Phe Ile Arg Val Val
1               5                  10                  15
Met Tyr Glu Gly Lys Lys Ile Met Ala Asp Ser Gly Pro Ile
                20                  25                  30
```

(2) INFORMATION FOR SEQ ID NO: 20:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO: 20:

```
Arg Trp Arg Leu Ser His Arg Pro Lys Thr Gly Phe Ile Arg Val Val
1               5                  10                  15
Met Tyr Glu Gly Lys Lys
                20
```

(2) INFORMATION FOR SEQ ID NO: 21:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 21:

```
Arg Trp Arg Leu Ser His Arg Pro Lys Thr Gly
1               5                  10
```

(2) INFORMATION FOR SEQ ID NO: 22:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 22:

```
Arg Pro Lys Thr Gly Phe Ile Arg Val
1               5
```

(2) INFORMATION FOR SEQ ID NO: 23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 23:

Arg Pro Lys Thr Gly Phe
1               5

(2) INFORMATION FOR SEQ ID NO: 24:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (xi) SEQUENCE DESCRIPTION: SEQ ID NO: 24:

Lys Thr Gly Phe Ile Arg
1               5

(2) INFORMATION FOR SEQ ID NO: 25:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (xi) SEQUENCE DESCRIPTION: SEQ ID NO: 25:

Tyr Glu Gly Lys Lys
1               5

(2) INFORMATION FOR SEQ ID NO: 26:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (xi) SEQUENCE DESCRIPTION: SEQ ID NO: 26:

Tyr Glu Gly Lys Lys Ile Met Ala Asp Ser Gly Pro Ile
1               5                   10

(2) INFORMATION FOR SEQ ID NO: 27:

(i) SEQUENCE CHARACTERISTICS:
          (A) LENGTH: 13 amino acids
          (B) TYPE: amino acid
          (D) TOPOLOGY: linear (ii) MOLECULE TYPE: peptide (xi) SEQUENCE DESCRIPTION: SEQ ID NO: 27:

Arg Phe Tyr Val Val Met Trp Lys Gln Val Thr Gln Ser
1               5                   10

(2) INFORMATION FOR SEQ ID NO: 28:

(i) SEQUENCE CHARACTERISTICS:
          (A) LENGTH: 12 amino acids
          (B) TYPE: amino acid
          (D) TOPOLOGY: linear (ii) MOLECULE TYPE: peptide (xi) SEQUENCE DESCRIPTION: SEQ ID NO: 28:

Arg Tyr Val Val Leu Pro Arg Pro Val Cys Phe Glu
1               5                   10

(2) INFORMATION FOR SEQ ID NO: 29:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 29:

Arg Tyr Val Val Leu Pro Arg
1               5

(2) INFORMATION FOR SEQ ID NO: 30:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 30:

Phe Ile Arg Val Val Met Tyr Glu Gly Lys Lys
1               5                   10

(2) INFORMATION FOR SEQ ID NO: 31:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 31:

Ser Ile Lys Val Ala Val Ser Ala Asp Arg
1               5                   10

(2) INFORMATION FOR SEQ ID NO: 32:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 32:

Phe Ile Arg Val Val Met Tyr Glu Gly Lys Lys
1               5                   10

(2) INFORMATION FOR SEQ ID NO: 33:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 33:

Tyr Ile Arg Val Val Met Tyr Glu Gly Lys Lys
1               5                   10

(2) INFORMATION FOR SEQ ID NO: 34:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO: 34:

Tyr Ile Arg Val Leu Val His Glu Gly Lys Gln
1               5                   10

(2) INFORMATION FOR SEQ ID NO: 35:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 35:

Tyr Met Arg Val Leu Val His Glu Gly Lys Gln
1               5                   10

(2) INFORMATION FOR SEQ ID NO: 36:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 36:

Leu Ile Lys Val Leu Val Tyr Glu Gly Lys Gln
1               5                   10

(2) INFORMATION FOR SEQ ID NO: 37:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 37:

Tyr Ile Arg Val Lys Leu Tyr Glu Gly Pro Gln
1               5                   10

(2) INFORMATION FOR SEQ ID NO: 38:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 38:

Tyr Ile Arg Val Arg Phe Tyr Glu Gly Pro Glu
1               5                   10

(2) INFORMATION FOR SEQ ID NO: 39:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 39:

Arg Phe Tyr Val Val Met Trp Lys Gln Val Thr
1               5                   10

(2) INFORMATION FOR SEQ ID NO: 40:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 40:

Arg Phe Tyr Val Val Met Trp Lys Gln Val Thr
1               5                   10

(2) INFORMATION FOR SEQ ID NO: 41:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 41:

Arg Phe Tyr Val Val Met Trp Lys Gln Val Thr
1               5                   10

(2) INFORMATION FOR SEQ ID NO: 42:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 42:

Arg Phe Tyr Val Val Met Trp Lys Gln Val Thr
1               5                   10

(2) INFORMATION FOR SEQ ID NO: 43:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 43:

Arg Phe Tyr Val Leu Met Trp Lys Gln Val Thr
1               5                   10

(2) INFORMATION FOR SEQ ID NO: 44:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 44:

```
Arg Phe Tyr Val Val Met Trp Lys Gln Thr Glu
1               5                   10
```

(2) INFORMATION FOR SEQ ID NO: 45:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 45:

```
Ser Phe Tyr Val Val Met Trp Lys Gln Met Glu
1               5                   10
```

(2) INFORMATION FOR SEQ ID NO: 46:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 46:

```
Phe Ile Arg Val Val Met Tyr Glu Gly Lys Lys
1               5                   10
```

(2) INFORMATION FOR SEQ ID NO: 47:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 47:

```
Phe Ile Arg Val Phe Ala Ile Leu Glu Asn Lys Lys
1               5                   10
```

US 6,469,138 B1

THROMBOSPONDIN RECEPTOR BINDING PEPTIDES

This is a DIVISION, of application Ser. No. 08/029,333, filed Mar. 5, 1993, now U.S. Pat. No. 5,399,667.

This invention was made with Government support under Grant No. HL4147 awarded by the National Institutes of Health. The Government has certain rights in the invention.

BACKGROUND OF THE INVENTION

The present invention relates to novel binding peptides and, more particularly, to small peptides that bind to the thrombospondin 1 receptor.

The interaction of cells with extracellular matrix (ECM) molecules is a complex process from which cells derive a wealth of information about their environment. This information is processed in a number of ways that ultimately affect cell motility, shape, proliferation and gene expression (Hynes, 1992). ECM macromolecules like fibronectin, laminin, vitronectin, and collagen have been shown to mediate cell adhesion, a process that includes cell attachment and spreading. Like these proteins, thrombospondin 1 (TS1) promotes adhesion of a number of normal and transformed cell types (Frazier, 1991; Roberts et al., 1987), a function which underlies many effects that TS1 exerts in several biologically complex systems. These effects include stabilizing platelet aggregation (Leung et al., 1984; Dixit et al., 1985), regulating cell growth (Majack et al., 1988; Good et al., 1990), specifying the differentiation phenotype of certain cells (Castle et al., 1991), wound healing (Raugi et al., 1987) and the migration of tumor cells (Tuszynski et al., 1987) and PMNs (Mansfield et al., 1990). A good example of the regulation of several aspects of cellular behavior by TS1 is the inhibition of angiogenesis in vivo and of endothelial cell migration and proliferation in vitro (Good et al, 1990; Taraboletti et al., 1990).

There are at least 4 TS isogenes, TS1, 2 and 3 (Bornstein et al., 1991; LaBell et al., 1992; Laherty et al., 1992; Vos et al., 1992) and cartilage oligomeric matrix protein or COMP (Oldberg et al., 1992) whose products are related, but decidedly different. Of these, platelet TS (which is pure TS1) is the best characterized, and serves as a prototype for this growing family. Distinct activities can be assigned to certain domains. For example, the amino-terminal domain of TS1 induces spreading of G361 cells while the COOH-terminal cell binding domain (CBD) of TS1 promotes haptotaxis and attachment of these cells (Taraboletti et al., 1987; Roberts et al., 1985). TS1 contains at least four domains that support cell attachment: the amino-terminal heparin-binding domain (Murphy-Ullrich et al., 1987), the type 1 repeats of about 60 amino acid residues containing a common subhexapeptide sequence (Prater et al., 1991), the RGD sequence in the last of the type 3 calcium binding repeats (Lawler et al., 1988) and the COOH-terminal ca. 220 residues termed the "cell-binding" domain (CBD, Kosfeld et al., 1991). Monoclonal antibody (MAb) called C6.7 which binds to this CBD and blocks its interaction with cellular receptors was previously described (Dixit et al., 1985). Using this MAb it has been shown that the CBD is essential for binding of TS1 to platelets (Dixit et al., 1985), many transformed cells (Varani et al., 1986) and to human melanoma cells (Taraboletti et al., 1987). The CBD of TS1 (rCBD) exclusive of the upstream RGD sequence has been expressed in bacteria and its attachment activity for human melanoma cells has been demonstrated (Kosfeld et al., 1991).

BRIEF DESCRIPTION OF THE INVENTION

In accordance with the present invention, novel small synthetic peptides are provided that bind to the thrombospondin 1 (TS1) receptor. These peptides preferably have 5–13 amino acid residues which share the tripeptide Val-Val-Met and have the following sequences:

RFYVVMWKQVTQS [SEQ ID NO:1] and fragments thereof containing the minimal sequence RFYVVM [SEQ ID NO:3], and FIRVVMYEGKK [SEQ ID NO:4] and fragments thereof containing the minimal sequence IRVVM [SEQ ID NO:5].

The novel VVM-containing peptides of the invention are illustrated by five preferred peptides in which the sequences are converted to the three-letter abbreviations and designated herein and in the Sequence Listing of the accompanying Diskette as f follows:

```
Arg Phe Tyr Val Val Met Trp Lys Gln Val Thr Gln Ser [SEQ ID NO:1]
                 5                   10

Arg Phe Tyr Val Val Met Trp Lys                      [SEQ ID NO:2]
                 5

Arg Phe Tyr Val Val Met                              [SEQ ID NO:3]
                 5

Phe Ile Arg Val Val Met Tyr Glu Gly Lys Lys          [SEQ ID NO:4]
                 5                   10

Ile Arg Val Val Met                                  [SEQ ID NO:5]
             5
```

The foregoing 5 illustrative peptides are also designated herein for structural purposes as 4N1, 4N1-1, 4N1-2, 7N3 and 7N3-1, respectively.

The novel binding peptides of this invention are contained in 2 non-overlapping 30-residue synthetic peptides, designated C4 and C7, respectively, of the thrombospondin 1 (TS1) COOH-terminal cell binding domain (CBD). These novel peptides retain the binding activity of the parent 30-mer peptides and faithfully reflect the binding activity of CBD.

These results were unexpected in view of the fact that, by way of distinction, the following closely related peptides were inactive in said binding:

Gly-Arg-Val-Val-Met [SEQ ID NO:6],
Ile-Glu-Val-Val-Met [SEQ ID NO:7] and
Ile-Arg-Val-Val-Gly [SEQ ID NO:8].

DETAILED DESCRIPTION OF THE INVENTION

While the specification concludes with claims particularly pointing out and specifically claiming the subject matter regarded as forming the present invention, it is believed that the invention will be better understood from the following preferred embodiments of the invention taken in conjunction with the accompanying drawings in which:

FIG. 1A shows the amino acid sequences of the subpeptides derived from peptide C4 of the CBD of TS1. The boxed letters indicate amino acid residues that are common in all active subpeptides.

FIG. 1B is a graphical representation which shows the direct attachment of G361 cells to C4 subpeptides. Equimolar concentrations of peptides shown in FIG. 1A were evaluated as attachment factors for G361 cells. Peptides C4 (⊠), 4N (●), 4N1 (▲), 4N1-1 (♦), 4N2 (■) and 4C (▯) were adsorbed to microtiter plates at the indicated concentrations. Cells were added to the wells and incubated for 1 hour at 37° C. The attached cells were quantitated as described under "Materials and Methods" hereinbelow, and the actual absorbance due to endogenous cellular phosphatase hydrolysis of p-Nitrophenyl phosphate at 410 nm is plotted.

FIG. 2A shows the amino acid sequences of subpeptides derived from peptide C7 of the CBD of TS1. The boxed letters indicate the amino acid residues that are in common in all active subpeptides.

FIG. 2B is a graphical representation which shows the direct attachment of G361 cells to subpeptides of peptide C7. Microtiter wells were adsorbed with peptides C7 (■), 7N (●), 7N3 (▲), 7N3-1 (♦), 7N2 (■), 7N2-2 (○), 7N3-2 (▲) and 7C, 7N1 or 7N2-1 (▯) at various concentrations and the attachment of G361 cells was determined. The numbers of cells attached to these peptides were correlated with the cellular phosphatase activity which is expressed as absorbance at 410 nm.

FIGS. 3A and 3B show the effect of the active subpeptides of C4 and C7 on G361 cell attachment to the rCBD of TS1. To microtiter wells containing immobilized rCBD (10 µg/ml), G361 cells were added with (FIG. 3A) 4N1-1 (●), 7N3-1 (■), 4N1-1 plus 7N3-1 (▲) and with (FIG. 3B) 4N1 (■), 7N3 (●) and 4N1 plus 7N3 (▲). The cells were incubated for 1.5 hr in the wells and cell attachment was determined. The effects of these subpeptides on cell attachment are expressed as percent relative to the maximum cell attachment for each test where 100% is the number of cells binding to rCBD-coated well in the absence of peptide inhibitors.

FIG. 4 shows cell attachment sites in TS1 and LM. Amino acid sequence comparison between a LM peptide designated LMF9 with 4N-1 and LM 22-2 with 7N3 is shown. Amino acid residues which are identical are shown in solid boxes while conservative substitutions are shown in broken boxes. The alignments produced were modified by the addition of a gap in the LMF9 in order to maintain the best alignment.

FIGS. 5A, 5B, 5C and 5D show the effects of soluble peptides of TS1 or LM on G361 cell attachment to immobilized TS1 or LM. (FIG. 5A) In the standard assay, G361 cells alone (no inhibitors) were added to microtiter wells coated with LM at the indicated concentrations. In inhibition studies, soluble subpeptides were included with G361 cells at the indicated concentrations. Soluble LM peptides LGTIPG, [SEQ ID NO:9], PGAIPG, [SEQ ID NO:10], YIGSR [SEQ ID NO:11], (■), LM1 (●), and LM2 (▲) were added to (FIG. 5B) LM-coated wells or (FIG. 5D) rCBD-coated surface. Soluble TS1 subpeptides 4N1-1 (■), 7N3-1 (▲), 4N1-1 plus 7N3-1 (●) were tested on (FIG. 5C) LM-coated wells. Control attachment (100%) is that with no added peptides. Data are shown for concentrations of each peptide below its solubility limit.

FIGS. 6A, 6B, 6C and 6D show the attachment of four cell types to immobilized TS-1 and LM. Wells were coated with the indicated concentrations of TS1 (■) or LM (●). Assays were performed as described under "Methods" hereinafter with (FIG. 6A)—G361 human melanomas; (FIG. 6B)—K562 erythroleukemia cells; (FIG. 6C)—HT1080 fibrosarcomas; and (FIG. 6D)—C32 amelanotic melanomas added to the wells.

Figure 7:
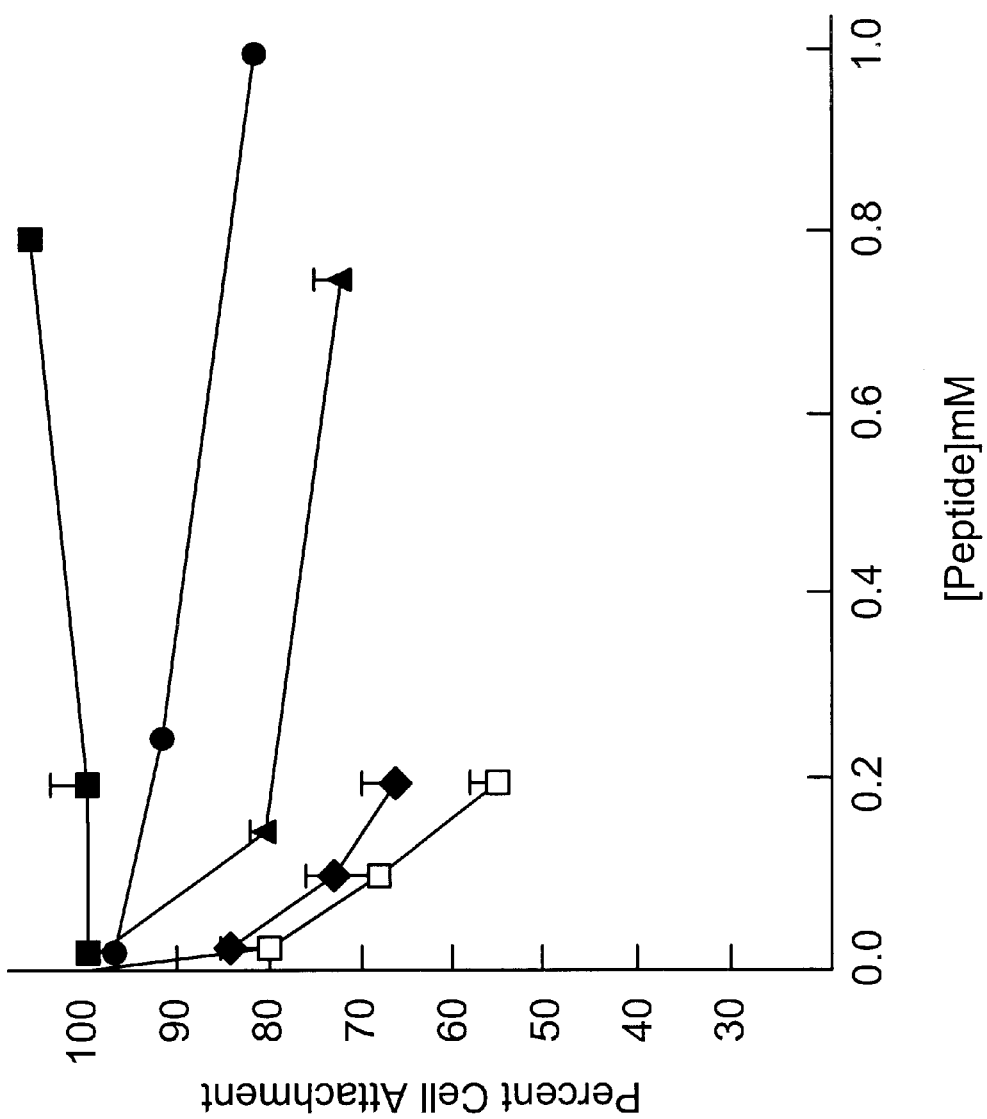

FIG. 7 is a graphical representation which shows the effect of peptides from TS1 and LM on K562 cell attachment to immobilized rCBD of TS1. Wells were coated with 10 µg/ml of rCBD/well. Prior to addition of K562 cells, indicated concentrations of peptide LM1 (■), LM2 (●), 4N-1 (♦), 7N3-1 (▲), and 4N1-1 plus 7N3-1 (⊠) were added to the wells. Control attachment (100%) is that with no added peptides.

FIGS. 8A and 8B show conserved cell-binding regions of the CBD of known TS1 isoforms. In FIG. 8A residues identical among the TS1 sequences are shown in the box. In FIG. 8B, only residues which differ are boxed. References for each sequence are indicated in the detailed description hereinafter.

FIG. 9A shows a region of human and mouse tenascin compared with peptide 7N3 of the CBD of TS1. Boxes enclose identical residues. FIG. 9B shows other extracellular proteins that contain sequences homologous to the 7N3-1 sequence of TS1, including IKVAV, [SEQ ID NO:12], IRVAV, [SEQ ID NO:13], and VRVAV [SEQ ID NO:14].

The novel binding peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoroacetate) and cyanogen bromide, and reaction in solution with isolation and purification of intermediates is well-known classical peptide methodology.

The preferred peptide synthesis method follows conventional Merrifield solid-phase procedures. See Merrifield, *J. Amer. Chem. Soc.* 85, 2149–54 (1963) and *Science* 150, 178–85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or p-methylbenz-hydrylamine polymer for synthesizing peptide amides. This method conveniently simplifies the number of procedural manipulations since removal of the excess reagents at each step is effected simply by washing the polymer.

Further background information on the established solid phase synthesis procedure can be had by reference to the treatise by Stewart and Young. "Solid Phase Peptide Synthesis," W. H. Freeman & Co., San Francisco, 1969, and the review chapter by Merrifield in *Advances in Enzymology* 32, pp. 221–296, F. F. Nold, Ed., Interscience Publishers, New York, 1969; and Erickson and Merrifield, *The Proteins,* Vol. 2, p. 255 et seq. (ed. Neurath and Hill), Academic Press, New York, 1976.

In order to illustrate the invention in further detail, the following specific laboratory examples were carried out with the results as indicated. Although specific examples are thus illustrated herein, it will be appreciated that the invention is not limited to these specific examples or the details therein. It will further be understood that the novel peptides of this invention are not limited to any particular method of synthesis.

EXAMPLES

Materials and Methods

The generation and characterization of mAB C6.7 and its epitope localization to peptide C7 within the CBD of TS1 were carried out by conventional published procedures (Dixit et al., 1985, Kosfeld et al., 1991). All cell lines used are conventional and were obtained by purchase from ATCC: human melanoma G361 (CRL 1424), K562 human erythroleukemia cells (ATCC CCL 241), HT-1080 human fibrosarcomas (ATCC CCL 121) and C32 amelanolic human melanoma (ATTC CRL 1585). Cells were cultured in RPM1 1640 medium supplemented with 10% fetal calf serum (FCS) at 5% $CO_2$ (Roberts et al., 1987). All reagents were obtained from Sigma Chemical Co. (St. Louis, Mo.) unless specified otherwise.

The rCBD of TS1—The rCBD was expressed by conventional procedures as previously described (Kosfeld et al., 1991). The rCBD was found in the soluble fraction of bacterial lysates, and was purified by chromatography on a column of Q-Sepharose "fast flow" (Pharmacia Fine Chemicals, Piscataway, N.J.) equilibrated with 50 mM Tris-HCl, pH 7.5, 0.15 M NaCl (TBS). The column was eluted with a linear gradient of NaCl (0.15–1 M) in the Tris buffer. Fractions with the highest concentration of the protein A-CBD fusion protein were identified by SDS-PAGE using 7.5% acrylamide gels, followed by staining with Coomassie Blue and western blotting using alkaline phosphatase-conjugated IgG to locate bands containing the protein A moiety. The rCBD fractions were dialyzed against PBS and stored at −70° C. until used. It is known that the protein A moiety has no attachment activity for these cells.

Peptide Synthesis—Peptides whose sequences correspond to portions of peptide C4 (FIG. 1A) or C7 (FIG. 2A) of the CBD of TS1 were synthesized and purified by conventional procedures as described previously (Prater et al., 1991). Briefly, peptides were made on an Applied Biosystems Model 3804 solid phase peptide synthesizer. The resultant peptides were cleaved and deblocked by Immuno-dynamics (San Diego, Calif.) and purified by reversed phase HPLC (Waters) using acetonitrile/0.1% TFA solvent systems. Purity was tested with analytical HPLC. Primary structures of peptides were confirmed by amino acid composition on a Beckman model 6300 amino acid analyzer, and by sequencing with an Applied Biosystems model 477A sequencer. All peptide preparations were tested for cytotoxicity on G361 cells and were not toxic at the concentrations employed in these tests.

Cell Adhesion Assay—Cell adhesion was performed in 96-well plates by conventional procedures as previously described (Prater et al., 1991; Kosfeld and Frazier, 1992). Synthetic peptides were solubilized with 6 N guanidine HCl (GnHCl) because some hydrophobic peptides were insoluble at concentrations approaching 1 mM in TBS. The peptides were coated onto plastic 96 well plates (Nunc Immuno Plate Maxisorp) by incubating 50 μl of peptide solutions per well at the indicated concentrations. After incubating overnight at room temperature, wells were rinsed with TBS and blocked with 10 mg/ml bovine serum albumin (BSA) for 30 minutes at room temperature. Peptides were also coupled to cyanogen bromide-activated Sepharose 4B (Pharmacia) according to the manufacturer's instructions. Approximately 2 mg of peptide was used per ml of the Sepharose. The efficiency of coupling of all peptides was greater than 90% as judged by UV absorbance. The peptide-coated beads were then blocked with BSA as above. IgG coated beads were also prepared for use as controls.

After blocking, cells were allowed to attach for 1 hr at 37° C. to substrate-coated wells or beads. In some tests, inhibition was determined by adding peptide inhibitors of cell attachment to each well along with the cells. After removal of non-adhering cells, cells attached to immobilized substrates were quantitated with endogenous cellular phosphatase activity which is measured by absorption at 410 nm as previously described (Prater et al., 1991). Each assay was carried out in duplicate and each peptide was tested in 3 separate tests at 3 or more different concentrations.

Peptide-BSA conjugates—In addition to the free peptides, peptides conjugated to protease-free BSA (Humphries et al., 1987) were also used in the cell binding assay. Peptides were synthesized with an N-terminal cysteine for covalent coupling to BSA via the heterobifunctional crosslinking reagent N-succinimidyl 3-(2-pyridyldithio) propionate (SPDP). BSA was activated at room temperature with SPDP at a molar ratio of 50:1 (SPDP:BSA) for 30 min. Unreacted SPDP was separated from derivatized BSA by gel filtration on a Sephadex G-25SF column equilibrated with PBS. The activated BSA was then added to dry peptide at a molar ratio of 1:20 (BSA:peptide). The reactants were mixed overnight at room temperature and unconjugated peptides removed by dialysis against PBS, pH 7.4. Peptide-BSA conjugates were stored frozen at −20° C. until used.

Results

The amino acid sequences of the subpeptides synthesized from C4 are shown in FIG. 1A. As a first step to locate the essential amino acid sequence(s) within C4, two peptides with overlapping sequences, 4N and 4C, were synthesized and their activities assessed using the cell attachment assay. The results in FIG. 1B show that peptide 4N, but not 4C, displayed high activity. In order to further locate the active sequence(s) within 4N, three shorter overlapping peptides spanning 4N (FIG. 1A) were tested. Peptide 4N1, Arg-Phe-Tyr-Val-Val-Met-Trp-Lys-Gln-Val-Thr-Gln-Ser [SEQ ID NO:1], showed significantly greater cell binding activity than peptide 4N2. 4N1-1, the amino-terminal sequence of 4N1, retained 60% of the maximum activity of 4N1. These results indicate the importance of the sequence common to both active peptides, 4N1 and 4N1-1, the novel octapeptide Arg-Phe-Tyr-Val-Val-Met-Trp-Lys [SEQ ID NO:2].

The amino acid sequences of the C7 subpeptides is shown in FIG. 2A and their cell attachment activities in FIG. 2B. First, two peptides, 7N and 7C, which together represent the entire length of C7 were synthesized. 7C actually extends beyond the C terminus of C7 (arrow in FIG. 2). The amino-terminal peptide, 7N, showed significant cell attachment activity while the COOH-terminal peptide, 7C, exhibited none. Next, 7N was divided into three overlapping subpeptides designated 7N1, 7N2, and 7N3. Of these, only 7N2 and 7N3 had significant activity, the activity of 7N2 being less than half of that of 7N3, Phe-Ile-Arg-Val-Val-Met-Tyr-Glu-Gly-Lys-Lys [SEQ ID NO:4]. Based on this result, 7N3 was further dissected into two pentapeptides, 7N3-1 and 7N3-2. Peptide 7N2 was also divided into two smaller subpeptides, 7N2-1 and 7N2-2. The 7N2-2 sequence contains the COOH-terminal sequence of the 7N2 and the amino-terminal sequence of the 7N3-1. The maximal cell attachment activity of 7N3-1 was comparable to that of 7N3, and nearly as high as that of 7N and the parent peptide C7. Peptides 7N2-1, 7N2-2 and 7N3-2 on the other hand, exhibited negligible attachment-promoting activities. These results localize the highest cell attachment activities to peptides containing the central region of C7 such as 7N, 7N3 and 7N3-1, indicating that the critical residues for activity lie in the 7N3-1 sequence. Thus both the aforesaid active octapeptide sequence from C4, and the pentapeptide sequence from C7, Ile-Arg-Val-Val-Met [SEQ ID NO:5], contain the VVM sequence, the only sequence shared by C4 and C7.

To ascertain that the activities of the peptides are not a function of their association with the plastic surface, peptides linked to BSA or Sepharose beads were also used in cell binding assays. Again the same peptides that are shown to be active in FIGS. 1 and 2 also promote substantial cell attachment when conjugated to BSA and then coated on plastic wells, or when covalently attached to Sepharose beads. These observations confirm the aforesaid sequences 4N1-1 from C4 and 7N3-1 from C7 as the primary determinants of the activity of the CBD of TS1.

To be sure that the active peptides from C4 and C7 contain the sequences that are relevant for attachment of cells to the CBD, the shorter, more soluble active peptides were tested as soluble inhibitors of the binding of G361 cells to rCBD immobilized on plastic wells. The short peptide, 7N3-1, in contrast to its larger homolog 7N3, is highly soluble, which makes it possible to test it at the high concentrations often required for inhibition of cell attachment. In contrast, 4N1-1 and 4N1, the active subpeptides for C4, are insoluble at concentrations higher than 0.2 mM and thus must be tested as soluble inhibitors at concentrations below this solubility limit. It should be noted that inclusion of peptides in the cell attachment assay at these concentrations had no adverse effects on the cells. The ability of the active subpeptides from C4 and C7 to inhibit G361 melanoma cell adhesion to rCBD is shown in FIG. 3. The results of this complementary bioassay confirmed those of the direct cell adhesion assays (FIGS. 1 and 2). It was found that peptides 4N1 and 7N3 interfere with the attachment of G361 cells to rCBD-coated surfaces by about 30% and 50%, respectively (FIG. 3B) while the shorter peptides 4N1-1 and 7N3-1 were inhibitory by 30% and 25%, respectively (FIG. 3A). The inhibition was dose-dependent at peptide concentrations <0.1 mM for 4N1 and 7N3 and <0.2 mM for 4N1-1 and 7N3-1. 7N3-1 tested at 2 mM exhibits no significant increase in inhibitory effect compared to that at 0.2 mM. Thus the shortest active subpeptides from C4 or C7, when added individually to cells, only partially inhibit cell attachment to the rCBD. A combination of these subpeptides however, had a synergistic effect as shown in the triangles in FIGS. 3A and 3B. Each peptide is present at ½ the indicated concentration. In the case of 4N1 plus 7N3, the inhibition was nearly complete (87%). In contrast, the effect of 4Nl-1 plus 7N3-1 was less than that of the longer 4N1 plus 7N3 peptides, suggesting that some active amino acid residues might be missing from the shorter peptides. In contrasting FIG. 3A to 3B, the activity exhibited by 4N1-1 and 4N1 was comparable while peptide 7N3-1 was not as active as 7N3. This suggests that 7N3-1 does not contain all of the active residues. To evaluate the contribution of adjacent sequences to activity, peptide 7N2-2 which contained the N-terminal sequence of 7N3-1, and 7N3-1 were examined in inhibition studies. While less inhibitory than 7N3-1, both peptides showed significant inhibitory activity, suggesting the importance of adjacent sequences in modifying the activity of the 7N3-1 peptide. Peptides that are distant from the active sequences of C4 and C7 (4C, 4N2, 7N1) showed no inhibition of cell attachment to the rCBD, indicating that the inhibition is specific and not due to cytotoxic effects of the peptide preparations.

In the course of these inhibition tests, a shorter peptide, Arg-Phe-Tyr-Val-Val-Met [SEQ ID NO:3], derived from 4N1-1 (designated 4N1-2) was tested. This hexapeptide had little or no activity in the direct cell adhesion assays (FIG. 1) yet in the inhibition assays was as potent as the longer 4N1-1. This may represent a case of a peptide that either binds very poorly to the plastic wells or, when bound, assumes a configuration on the plastic that prevents it from interacting with cellular receptors. Peptides which alter the sequence of 7N3-1 were also synthesized to test the importance of the isoleucine, arginine and methionine residues in binding to cellular receptors. These peptides, Gly-Arg-Val-Val-Met [SEQ ID NO:6], Ile-Glu-Val-Val-Met [SEQ ID NO:7] and Ile-Arg-Val-Val-Gly [SEQ ID NO:8] were tested as inhibitors of cell adhesion to the rCBD. All were inactive.

The aforesaid octapeptide 4N1-1 and pentapeptide 7N3-1 were thus identified as important sequences for the cell attachment activity of the TS1 CBD. Further, the hexapeptide 4N1-2 is active as an inhibitor of cell binding to the rCBD. These peptides share the tripeptide VVM and both contain an arginine upstream. Search was then made for sequences related to these peptides in other cell adhesion and ECM proteins (Yamada, 1991). This search revealed two peptides from laminin (LM) having sequences similar to 4N1 and 7N3. The sequence homology between these peptides is shown in FIG. 4. The peptide designated LMF9, from the F9 fragment of LM (Skubitz et al., 1990), shares 5 identical residues and 2 conservative substitutions with 4N1. LM22-2, from peptide PA22.2 of LM (Tashiro et al., 1989), has sequence homology (not identity) with 7N3, particularly within the LM-2 active region of the LM peptide. Two peptides modeled on these residues of LM (FIG. 4) were synthesized and tested as substrates for attachment of G361 cells. LM-1 (the LMF9 analog of TS1 4N1-1) had little cell attachment activity while LM-2 (the PA22-2 analog of TS1 7N3-1) bound cells but to a lesser degree than the 7N3-1. These results were confirmed using peptides linked to BSA and Sepharose beads.

The ability of these peptide homologs to substitute for each other in inhibiting G361 cell binding to the TS1 rCBD or LM-coated surfaces (FIG. 5) was also tested. G361 cells bound to LM in a concentration-dependent manner (FIG. 5A) and this attachment activity was inhibited by LM1 (21%), LM2 (28%) (FIG. 5B), 4N1-1 (32%) and 7N3-1 (50%) (FIG. 5C). LM1 and LM2 also inhibited cell binding to the CBD of TS1, 15% and 34%, respectively (FIG. 5D). Quantitatively, LM peptides were less effective than their TS1 homologs. Other adhesive peptides of LM were also tested as inhibitors of the CBD and LM but showed no detectable activity (FIGS. 5B and 5D). These results suggest that TS1 and LM may be able to share a common receptor.

To further address this issue, several cell types and lines were tested for attachment to LM and TS1 to see if any cells attached to one protein but not the other. FIG. 6 shows attachment to TS1 and LM of four cell types. These include G361 human melanomas (FIG. 6A). K562 human erythroleukemia cells (FIG. 6B), HT1080 human fibrosarcomas (FIG. 6C) and C32 human melanoma (FIG. 6D). It is of interest to note that C32 and K562 cells attached to TS1 much more avidly than to LM while G361 and HT1080 cells bound well to both proteins. The K562 cells also bound well to the rCBD and its active sequences. Next the effect of 4N1-1, 7N3-1 and their LM homologs on K562 cell attachment to the rCBD was tested. Since these cells demonstrated specific attachment to TS1 and not to LM, no LM receptor should contribute to the binding of the TS1 CBD. As follows from the previous results, the TS1 peptides showed significant inhibitory activity (36% for 4N1-1, 28% for 7N3-1) while the LM peptides exhibited an undetectable (LM1) or a lower (19% for LM2) level of inhibition (FIG. 7). In agreement with previous results, the combination of 4N1-1 and 7N3-1 increased the inhibition of rCBD-mediated cell attachment (45%). The TS1 peptides thus, are better competitors than the LM peptides in the absence of a LM receptor interaction. K562 cells therefore provide a valuable model in which only the cellular interactions with TS1 can be evaluated. Thus it appears that a receptor exists which binds the rCBD of TS1 with a high degree of specificity which excludes an interaction with LM.

Based on the assumption that the active sequences in the CBD are critical for cell attachment, it would appear that these residues would be conserved among different species. FIG. 8 shows the alignment of the homologs of peptides 7N3 and 4N1 from all known isoforms and species of TS. While peptide 7N3 is highly conserved only in human and mouse TS1, similar residues are retained in human, mouse and chicken TS2. In mouse TS3 and in bovine and rat COMP, positively charged residues are rearranged. Peptide 4N1, however shows an extremely high degree of conservation in all species and isoforms of TS sequenced to date. In fact within the region of the shortest active peptide, 4N1-1, there are only two substitutions in all known sequences. This conservation of sequence indicates that this is a region of the TS1 CBD responsible for a critical function that may be retained through evolution and in various TS isoforms.

The sequences 4N1-1, 7N3 and 7N3-1 were used as probe sequences in a computer search of all available data bases. No perfect matches were found for the octapeptide 4N1-1 sequence or its shorter inhibitory hexapeptide form 4N1-2. Similarly, the 7N3-1 pentapeptide sequence appears to be unique to TS1 isoforms among extracellular proteins. However, searching for homologs of the 7N3 sequences revealed that human and mouse tenascin contain a related sequence shown in FIG. 9. Since evidence has been obtained (above) that the LM sequence LM-2 can at least partially substitute for the TS1 sequence 7N3-1, a search was made for combinatiorially interchanged sequences. As shown in FIG. 9B, several interesting extracellular proteins contain related sequences including human and mouse LM, human and porcine von Willebrand factor, porcine factor VIII and rat α-2-macroglobulin. These proteins have been singled out because they interact with cells through receptors, some of which have not yet been identified. It is believed that the TS1 homologous sequences represent occurrences of a similar receptor binding motif in these proteins. These novel sequences are as follows:

```
Ile Arg Val Ala Val        [SEQ ID NO:13]     and
                5

Val Arg Val Ala Val        [SEQ ID NO:14].
                5
```

Amino acids are shown herein either by standard one letter or three letter abbreviations as follows:

| Abbreviated Designation | | Amino Acid |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

References shown in parentheses herein are appended at the end.

Various other examples will be apparent to the person skilled in the art after reading the present disclosure without departing from the spirit and scope of the invention. It is intended that all such other examples be included within the scope of the appended claims.

References

Asch, A. S., Bamwell, J., Silverstein, R. L, and Nachman, R. L (1987) *J. Clin. Invest* 79, 1054–1061

Aufderheide, E., Chiquet-Ehrismann, R. and Ekblom, R. (1987) *J. Cell Biol.* 105, 599–608

Bornstein, P., O'Rourke, K., Wikstrom, K., Wolf, F. W., Katz, R., Li, P., and Dixit, V. M. (1991) *J. Biol. Chem* 266,12821–12824

Bomstein, P. (1992) *FASEB J.* 6, 3290–3299

Bourdon, M. A., and Ruoslahti, E (1989) *J. Cell Biol.* 108,1149–1155

Bowditch, R. D., Halloran, C. E., Aota, S-i., Obara, M., Plow, E. F., Yamada, K. M., and Ginsberg, M. H. (1991) *J. Biol. Chem.* 266, 23323–23328.

Castle, V., Varani, J., Fligiel, S., Prochoronik, E. V. and Dixit, V. M. (1991) *J. Clin. Invest* 87,1883–1888

Chiquet-Ehrismann, R., Kalla, P., Pearson, C. A., Beck, K. and Chiquet M. (1988) *Cell* 53, 383–390

Chiquet-Ehrismann, R., Mackie, E. J., Person, C. A. and Sakakura. T. (1986) *Cell* 47, 131–139

Dixit, V. M., Haverstack, D. M., O'Rourke, K. M., Hennessy, S. W., Broekelmann, T. J., McDonald, J. A., Grant, G. A., Santoro, S. A., and Frazier, W. A. (1985) *Proc. Natl. Acad. Sci. USA* 82, 3472–3476

Erickson, P., and Bourdon, M. A. (1989) *Ann. Rev. Cell Biol.* 5, 71–92

Frazier, W. A. (1991) *Cur. Op. in Cell Biol.* 3, 793–799

Good, D. J., Polverini, P. J., Rastinejad, F., Le Beau, M. M., Lemons R. S., Frazier, W. A., and Bouck, N. P. (1990) *Proc. Natl. Acad. Sci. USA* 87, 6624–6628.

Humphries, M. J., Komoriya, A., Akiyama, S. K., Olden, K., and Yamada K. M. (1987) *J. Biol. Chem.* 262, 6886–6892

Hynes, R.O. (1992) *Cell* 69, 11–25

Komoriya, A., Green, L. J., Mervic, M., Yamada, S. S., Yamada, K. M., and Humphries, M. J. (1991) *J. Biol. Chem.* 266, 15075–15079

Kosfeld, M. D. and Frazier, W. A. (1992) *J. Biol. Chem.* 267, 16230–16236

Kosfeld, M. D., Paviopoulos, T. V., and Frazier, W. A. (1991) *J. Biol. Chem* 266, 24257–24259

LaBell, T. L., McGookey-Milewicz, D. J., Disteche, C. M. and Byers, P. H. (1992) *Genomics* 12, 421–429.

Laherty, C. D., O'Rourke, K., Wolf, F. W., Katz, R., Seldin, M. F. and Dixit, V. M. (1992) *J. Biol. Chem.* 267, 3274–3281

Lawler, J., Weinstein, R., and Hynes, R. O. (1988) *J. Cell. Biol.* 107, 2351–2361

Leung, L. L. K. (1984) *J. Clin. Invest.* 74, 1964–1972

Lotz, M. M., Burdsal, C. A., Erickson, H. P. and McClay, D. R. (1989) *J. Cell Biol.* 109, 1795–1805

Mackie, E. J., Halfter, W., and Liverani, D. (1988a) *J. Cell Biol.* 107, 2757–23767

Mackie, E. J., Chiquet-Ehrismann, R., Pearson, C. A., Inaguma, Y., Taya K., Kawarada, Y., and Sakakura, T. (1987) *Proc. Natl. Acad. Sci. USA* 84, 4621–4625

Majack, R. A., Cook, S. C. and Bomstein P. (1985) *J. Cell Biol.* 101, 1059–1070

Majack, R. A., Mildbrandt, J. and Dixit, V. M. (1987) *J. Biol. Chem* 262, 8821–8825

Majack, R. A., Goodman, E. and Dixit, V. M. (1988) *J. Cell Biol.* 106, 415–422

Manfield, P. J., Boxer, L. A. and Suchard, S. J. (1990) *J. Cell Biol.* 111, 3077–3086

Murphy-Ullrich, J. E. and Hook, M. (1989) *J. Cell Biol.* 109, 1309–1319

Oldberg, A., Antonsson, P. Lindblom, K., and Heinegard, D. (1992) *J. Biol. Chem.* 267, 22346–22350

Prater, A. C., Plotkin, J., Jaye D., and Frazier, W. A. (1991) *J. Cell Biol.* 112,1031–1040.

Raugi, G. J., Olerud, J. E., and Gown, A. M. (1987) *J. Invest. Dermatol.* 89, 551–554

Roberts, D. D., Sherwood, J. A., and Ginsburg, V. (1987) *J. Cell Biol.* 104, 131–139.

Sage, E. H. and Bomstein, P. M. (1991) *J. Biol. Chem* 266,14831–14834

Skubitz, A. P. N., McCarthy, J. B., Zhao, W., Yi, X-Y. and Furcht, L. T. (1990) *Cancer Res.* 50, 7612–7622

Spring, J., Beck, K., and Chiquet-Ehrismann, R. (1989) *Cell* 59, 325–334

Sun, X., Mosher, F., and Rapraeger, A. (1989) *J. Biol. Chem.* 264, 2885–2889

Taraboletti, G., Roberts, D. D., and Uotta, L. A. (1987) *J. Cell Biol.* 105, 2409–2415.

Taraboletti, G., Roberts, D. D., Liotta, L. A. and Giavazzi, R. (1990) *J. Cell Biol.* 111, 765–772

Tashiro, K-i., Sephel, G. C., Weeks, B., Sasaki, M., Martin, G. R., Kleinman, H. K., and Yamada, Y. (1989) *J. Biol. Chem.* 264, 16174–16182

Tuszynski, G. P., Gasic, T. B., Rothman, V. L., Knudsen, K. A., and Gasic, G. J. (1987) *Cancer Res.* 47, 4130–4133

Ullrich, A. and Schiessinger, J. (1990) *EMBO J.* 10, 2849–2854

Varani, J., Dixit V. M., Fligiel, E. G., McKeever, P. E., and Carey, T. E. (1986) *Exp. Cell Res.* 167, 376–390.

Vos, H. L., Devarayalu, S., deVries, Y. and Bomstein, P. (1992) *J. Biol. Chem.* 267, 12192–12196

Yamada, K. M. (1991) *J. Biol. Chem.* 266, 12809–12812.

What is claimed is:

1. A peptide that binds to the thrombospondin 1 receptor and having the sequence Ile Arg Val Ala Val [SEQ ID NO:13].

2. A peptide that binds to the thrombospondin 1 receptor and having the sequence Val Arg Val Ala Val [SEQ ID NO:14].

* * * * *